United States Patent
Podany

(10) Patent No.: US 7,066,895 B2
(45) Date of Patent: Jun. 27, 2006

(54) ULTRASONIC RADIAL FOCUSED TRANSDUCER FOR PULMONARY VEIN ABLATION

(75) Inventor: Vaclav O. Podany, New Fairfield, CT (US)

(73) Assignee: Ethicon, Inc., Somerville, NJ (US)

( * ) Notice: Subject to any disclaimer, the term of this patent is extended or adjusted under 35 U.S.C. 154(b) by 108 days.

(21) Appl. No.: 10/609,693

(22) Filed: Jun. 30, 2003

(65) Prior Publication Data

US 2004/0267132 A1    Dec. 30, 2004

(51) Int. Cl.
*A61H 1/00* (2006.01)
(52) U.S. Cl. .......................................... 601/3
(58) Field of Classification Search ................ 600/439, 600/459, 471; 601/2–4; 606/1
See application file for complete search history.

(56) References Cited

U.S. PATENT DOCUMENTS

| | | | |
|---|---|---|---|
| 4,142,412 A * | 3/1979 | McLeod et al. ......... 73/861.25 |
| 5,630,837 A * | 5/1997 | Crowley ........................ 601/2 |
| 6,461,314 B1 * | 10/2002 | Pant et al. ..................... 601/2 |
| 6,514,249 B1 * | 2/2003 | Maguire et al. .............. 606/41 |
| 6,669,655 B1 * | 12/2003 | Acker et al. .................... 601/2 |
| 6,672,312 B1 * | 1/2004 | Acker ........................ 128/898 |
| 6,685,640 B1 * | 2/2004 | Fry et al. ..................... 600/439 |
| 6,752,805 B1 * | 6/2004 | Maguire et al. .............. 606/41 |
| 6,758,847 B1 * | 7/2004 | Maguire ....................... 606/41 |
| 6,869,431 B1 * | 3/2005 | Maguire et al. .............. 606/41 |
| 2002/0068885 A1 * | 6/2002 | Herhen et al. ................. 601/3 |
| 2003/0120268 A1 | 6/2003 | Bertolero et al. |
| 2004/0116921 A1 | 6/2004 | Sherman et al. |

* cited by examiner

Primary Examiner—Francis J. Jaworski

(57) ABSTRACT

A method for ablating tissue with ultrasonic energy is provided. The method including: generating ultrasonic energy from one or more ultrasonic transducers; and focusing the ultrasonic energy in the radial direction by one of: shaping the one or more ultrasonic transducers to focus ultrasonic energy in the radial direction; and arranging one or more lenses proximate the one or more ultrasonic transducers for focusing the ultrasonic energy from the one or more ultrasonic transducers in a radial direction.

15 Claims, 4 Drawing Sheets

ULTRASONIC RADIAL FOCUSED TRANSDUCER FOR PULMONARY VEIN ABLATION

BACKGROUND OF THE INVENTION

1. Field of the Invention

The present invention relates generally to ultrasonic medical instrumentation, and more particularly, to an ultrasonic radial focused transducer for pulmonary vein (PV) ablation.

2. Prior Art

Ultrasonic transducers are used in medical instrumentation for ablation of the pulmonary veins of the heart. A distal end of such an instrument is shown in FIG. 5, generally referred to by reference numeral 100. The instrument 100 has an outer sheathing 102 having an ultrasonic transducer 104 housed therein. The ultrasonic transducer 104 is operatively connected to an ultrasonic generator (not shown) by wiring. The ultrasonic generator may be integrally formed with the instrument or remote therefrom. The acoustic energy (alternatively referred to as ultrasonic energy or an ultrasonic wave) emanating from the ultrasonic transducer 104 is shown throughout this disclosure by dashed lines A. To fit within the geometry of the pulmonary vein, the ultrasonic transducer 104 is cylindrical in shape and can be hollow to create an air backing, as is known in the art. The acoustic intensity of the ultrasonic wave generated by the cylindrical transducer decreases with the distance from its surface (e.g., in the radial direction R as shown in FIG. 6). In the pulmonary vein ablation, the acceptable diameter of the ultrasonic transducer 104 is also limited by the application and the approach taken so that the initial power available is also limited. As a result, the acoustic energy generated by the small diameter cylindrical transducer 104 is too low at the surface of larger diameter pulmonary veins, which can be as large as 35 mm in diameter. Therefore, the acoustic energy available is not sufficient to properly ablate the surface of the larger pulmonary veins.

SUMMARY OF THE INVENTION

Therefore it is an object of the present invention to provide ultrasonic devices and methods for their use, which overcome the disadvantages of conventional ultrasonic instrumentation known in the art.

Accordingly, a first embodiment of an ultrasonic instrument for ablation of tissue is provided. The first embodiment of the ultrasonic instrument comprising one or more ultrasonic transducers, the one or more ultrasonic transducers being shaped to focus ultrasonic energy in a radial direction.

The one or more ultrasonic transducers can comprise two ultrasonic transducers, each of the two ultrasonic transducers having a shape of a truncated cone having a truncated end, the truncated end from each of the two ultrasonic transducers being arranged to face each other. The truncated ends can be separated by a predetermined distance to form a gap. Further, a cylindrical ultrasonic transducer can be disposed in the gap. The cylindrical ultrasonic transducer can have a length substantially equal to the predetermined distance. Alternatively, the truncated ends can be separated by a variable distance to form a gap.

The one or more ultrasonic transducers can comprise two ultrasonic transducers separated by a gap, where the ultrasonic instrument further comprises means for varying the length of the gap.

In a first variation of the ultrasonic instrument for ablation of tissue according to the first embodiment, the ultrasonic instrument can comprise: a body having a distal end; one or more ultrasonic transducers, the one or more ultrasonic transducers being shaped to focus ultrasonic energy in a radial direction; and an ultrasonic generator operatively connected to the one or more ultrasonic transducers.

In a second variation of the ultrasonic instrument according to the first embodiment, the ultrasonic instrument can comprise: a body having a distal end; and one or more ultrasonic transducers, the one or more ultrasonic transducers being shaped to focus ultrasonic energy in a radial direction.

Also provided is a second embodiment of an ultrasonic instrument for ablation of tissue. The second embodiment of the ultrasonic instrument comprising: an ultrasonic transducer; and one or more lenses for focusing ultrasonic energy from the ultrasonic transducer in a radial direction.

The ultrasonic transducer can be cylindrical. The one or more lenses can be a single concave lens that surrounds the cylindrical ultrasonic transducer. The second embodiment of the ultrasonic instrument can further comprise a body for housing the one or more ultrasonic transducers, the body having a sidewall proximate the one or more ultrasonic transducers, the one or more lenses being integral with at least a portion of the sidewall.

Also provided is an ultrasonic instrument comprising: one or more ultrasonic transducers for transmitting ultrasonic energy in at least a radial direction; and focusing means for focusing the ultrasonic energy from the one or more ultrasonic transducers in the radial direction, wherein the focusing means is one of: shaping the one or more ultrasonic transducers to focus the ultrasonic energy in the radial direction; and one or more lenses for focusing the ultrasonic energy from the one or more ultrasonic transducers in a radial direction.

Still provided is a method for ablating tissue with ultrasonic energy where the method comprises: generating ultrasonic energy from one or more ultrasonic transducers; and focusing the ultrasonic energy in the radial direction by one of: shaping the one or more ultrasonic transducers to focus ultrasonic energy in the radial direction; and arranging one or more lenses proximate the one or more ultrasonic transducers for focusing the ultrasonic energy from the one or more ultrasonic transducers in a radial direction.

The one or more ultrasonic transducers can comprise two ultrasonic transducers and the shaping can comprise providing each of the two ultrasonic transducers in a shape of a truncated cone having a truncated end, the truncated end from each of the two ultrasonic transducers being arranged to face each other.

The method can further comprise separating the truncated ends by a predetermined distance to form a gap and disposing a cylindrical ultrasonic transducer in the gap. The method can further comprise varying the distance between the truncated ends. The one or more lenses can be a single concave lens, the one or more ultrasonic transducers can be a cylindrical ultrasonic transducer, and the arranging can comprise surrounding the cylindrical ultrasonic transducer with the single concave lens. The method can further comprise a body for housing the one or more ultrasonic transducers, the body having can have a side wall proximate the one or more ultrasonic transducers, and the surrounding can comprise integrally forming the one or more lenses with at least a portion of the side wall. The method can further comprise inserting at least a portion of the one or more ultrasonic transducers into a pulmonary vein of the heart prior to or simultaneous with the generating. The one or more ultrasonic transducers can be enclosed in an inflatable balloon, and the method can further comprise inflating the balloon to fix the one or more ultrasonic transducers in a predetermined position in the pulmonary vein.

The method can further comprise varying the distance to which the ultrasonic energy is focused in the radial direction.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of surgical procedures, it has been found particularly useful in the environment of ablation of the pulmonary vein. Therefore, without limiting the applicability of the invention to ablation of the pulmonary veins, the invention will be described in such environment.

Figure 1:
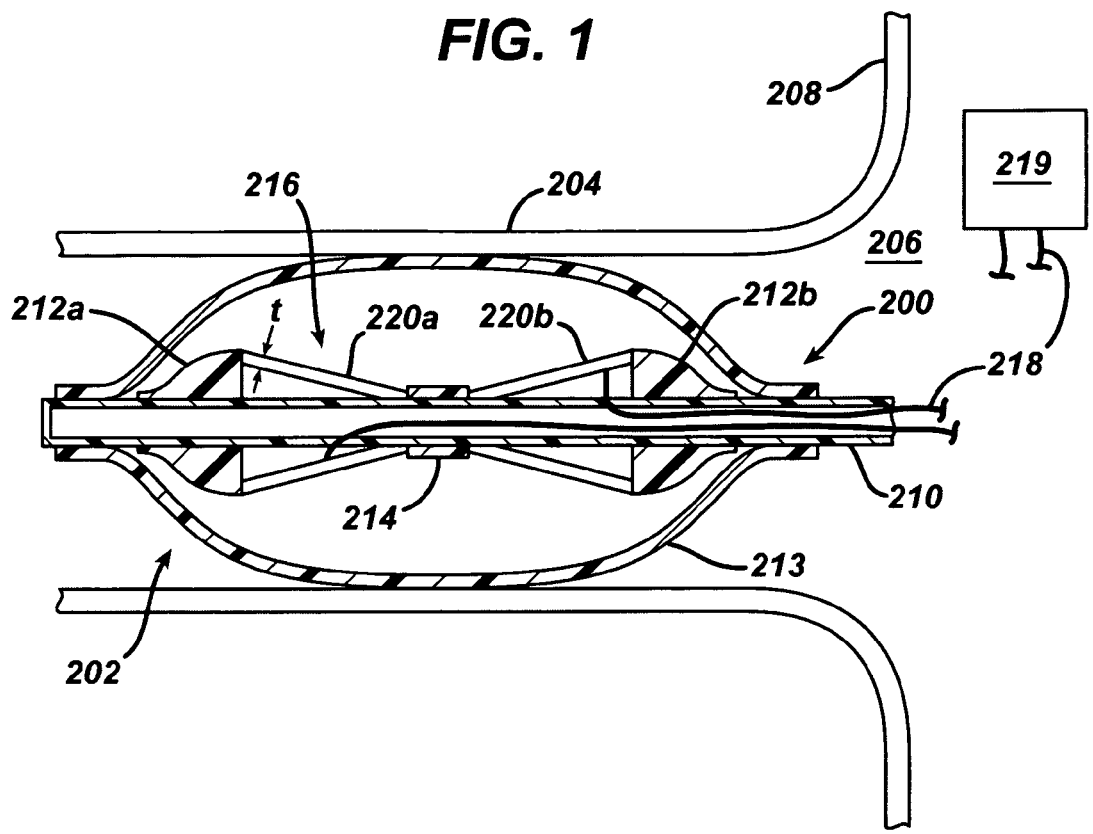
FIG. 1 illustrates a sectional view of a distal end of an ultrasonic instrument shown disposed in a pulmonary vein of the left atrium of the heart.

Referring now to FIG. 1, there is shown a first embodiment of an ultrasonic instrument for ablation of tissue, the ultrasonic instrument is generally referred to herein with reference numeral 200. A distal end 202 of the instrument 200 is shown disposed in a pulmonary vein 204 by way of the left atrium 206 of the heart 208. The ultrasonic instrument 200 can be configured in any number of ways known in the art, however, when accessing the pulmonary vein 204, it is preferred to be configured as a rigid device having an articulating distal end 202 which accesses the pulmonary vein through a puncture/access port in the heart wall (which is closed after the procedure). Preferably, the rigid ultrasonic instrument 200 will have a 12–15" long shaft operatively connected to the distal end 202 and a handle at a proximal end of the shaft. The ultrasonic instrument 200 can also be configured as a flexible catheter and introduced into the heart in any manner known in the art, such as by catherization of the heart.

The ultrasonic transducer generally has a body 210. Since the diameter of the instrument 200 is preferably approximately 3 to 4 mm in diameter and the inside diameter of the pulmonary vein is approximately 25 to 35 mm, the body may have an inflatable balloon 213 which when inflated positions the instrument 200 in the mouth of the pulmonary vein 204 and fixes it in position. The balloon 213 is preferably expanded by filling it with a medium, such as water or saline from an appropriate source (not shown).

The ultrasonic instrument 200 comprises one or more ultrasonic transducers 216 housed in or on the body 210 (collectively referred to herein as housed in the body). The one or more ultrasonic transducers 216 are operatively connected to an ultrasonic generator 219 for generating acoustic energy to ablate tissue. The ultrasonic generator 219 may be integrally housed within the instrument or remotely connected through wiring 218. FIG. 1 shows two such ultrasonic transducers 220a and 220b by way of example only. The ultrasonic transducers 220a, 220b are shaped to focus ultrasonic energy A in a radial direction R. As will be discussed below, more than two may be provided or a single integrally formed ultrasonic transducer may also be provided having a shape which focuses the ultrasonic energy A in the radial direction R. However, those skilled in the art will appreciate that two or more such ultrasonic transducers are preferred for their ease of fabrication.

Figure 2:
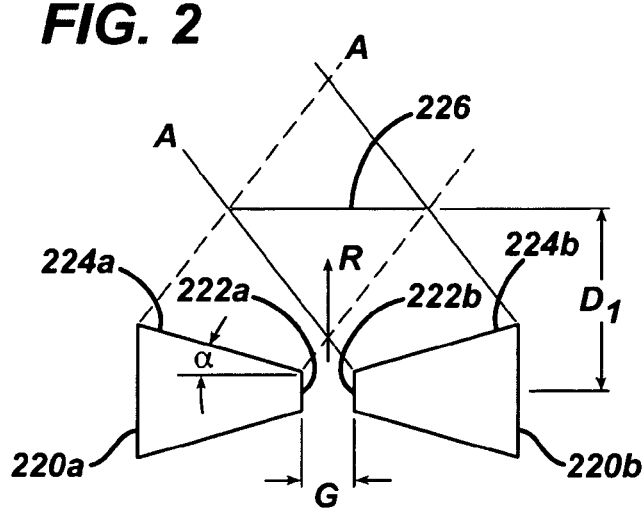
FIG. 2 illustrates a schematic view of the ultrasonic transducers of the instrument of FIG. 1.

Referring now to FIGS. 1 and 2 in combination, each of the ultrasonic transducers 220a and 220b can have a shape of a truncated cone having a truncated end 222a, 222b where the truncated ends 222a, 222b from each of the two ultrasonic transducers 220a, 220b are arranged to face each other. In FIG. 2, the ultrasonic transducers 220a, 220b are shown schematically outside the body 210 of the instrument 200 for illustration purposes only. The ultrasonic energy A from ultrasonic transducer 220a is shown as a dotted line, while the ultrasonic energy A from ultrasonic transducer 220b is shown as a solid line. Only one plane of ultrasonic energy A in the radial direction R is shown in the Figures, however, those skilled in the art will appreciate that the ultrasonic energy A irradiates in all radial directions around the circumference of the ultrasound transducers 220a, 220b. Furthermore, although the ultrasound transducers 220a, 220b are shown as truncated cones, those skilled in the art will appreciate that other shapes which focus the ultrasound energy A in the radial direction R are possible. The ultrasound transducers 220a, 220b may be hollow to provide an air backing, as is known in the art, which may also be used for routing the wiring 218. However, if transducers 220a, 220b are hollow, their wall thickness t should be constant along the length of the transducers 220a, 220b. If the wall thickness varies, only a small part of the transducer would emit an appreciable amount of energy which may not be sufficient for creating a lesion. The ultrasound transducers 220a, 220b may be fixed in the distal portion 212 of the body 210 by any means known in the art, such as with caps 212a, 212b and/or adhesive. Furthermore, a spacer 214 may be provided between the transducers 220a, 220b.

As shown in FIG. 2, the ultrasonic energy A from each of the ultrasound transducers 220a, 220b, irradiate perpendicular to the conic surface 224a, 224b. The conic surfaces 224a, 224b are shown to be linear, however, such surfaces may also be concavely and/or convexly shaped and may also include linear sections. If the conic surfaces 224a, 224b are curved, as discussed above, the wall thickness t should be maintained constant which may be very difficult to fabricate.

Figure 5:
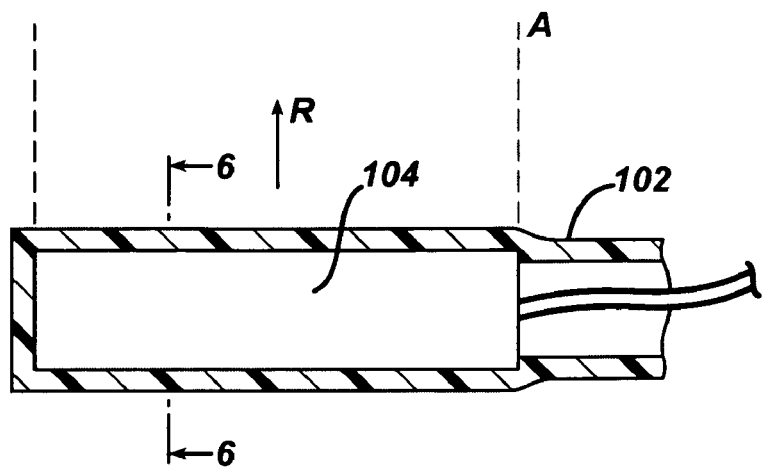
FIG. 5 illustrates a sectional view of a distal end of an ultrasonic instrument of the prior art.
Figure 6:
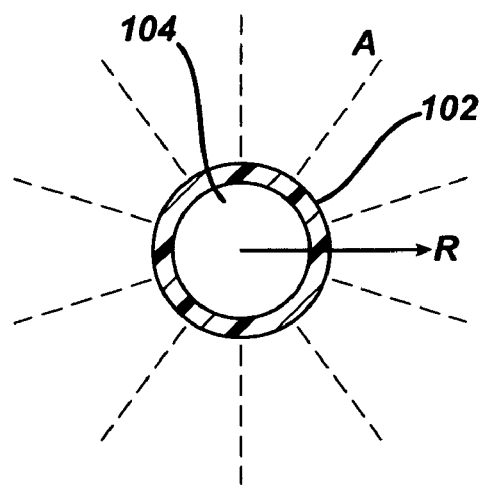
FIG. 6 illustrates a sectional view of the instrument of FIG. 5 as taken along line 6—6 in FIG. 5.

The energy A from each of the ultrasound transducers 220a, 220b, intersect at line 226 which is rotated 360 degrees around the ultrasound transducers 220a, 220b to form a cylinder of focused energy. The line 226 of focused ultrasonic energy is at a distance D1 from the center of the ultrasound transducers 220a, 220b and is greater than the ultrasound energy from a similarly sized cylindrical transducer of the prior art (see FIG. 5). The distance D1 is a function of the geometry of the one or more ultrasound transducers 216 including the angle α that the conic surfaces 224a, 224b make with the center of the ultrasound transducers 220a, 220b and the length of the gap G between the ultrasound transducers 220a, 220b. Since the balloon 213 is filled with a medium for expanding the balloon 213, such as water or saline, the flow of blood is blocked and the ultrasonic energy is not directed through blood that could potentially create blood clots at a hot surface of the pulmonary vein. Additionally, the water or saline provides an acoustic coupling to transmit the ultrasonic energy from the transducers 220a, 220b. Furthermore, the water or saline provides cooling to the tissue and the transducers 220a, 220b. Preferably, the transducers 220a, 220b are in direct contact with the water or saline (e.g., there is no sheath over the transducers 220a, 220b) to increase the efficiency by which the water or saline cools the transducers 220a, 220b. The water or saline can be re-circulated through the balloon 213 to increase the cooling efficiency.

Those skilled in the art will appreciate that these factors can be varied to provide a focusing distance D1 appropriate for various diameter pulmonary veins 204. Those skilled in the art will also appreciate that the length of the gap G may be made variable with simple mechanisms known in the art, thus eliminating the need for manufacturing instruments 200 corresponding to various focusing distances D1 for various pulmonary vein geometries.

Figure 7:
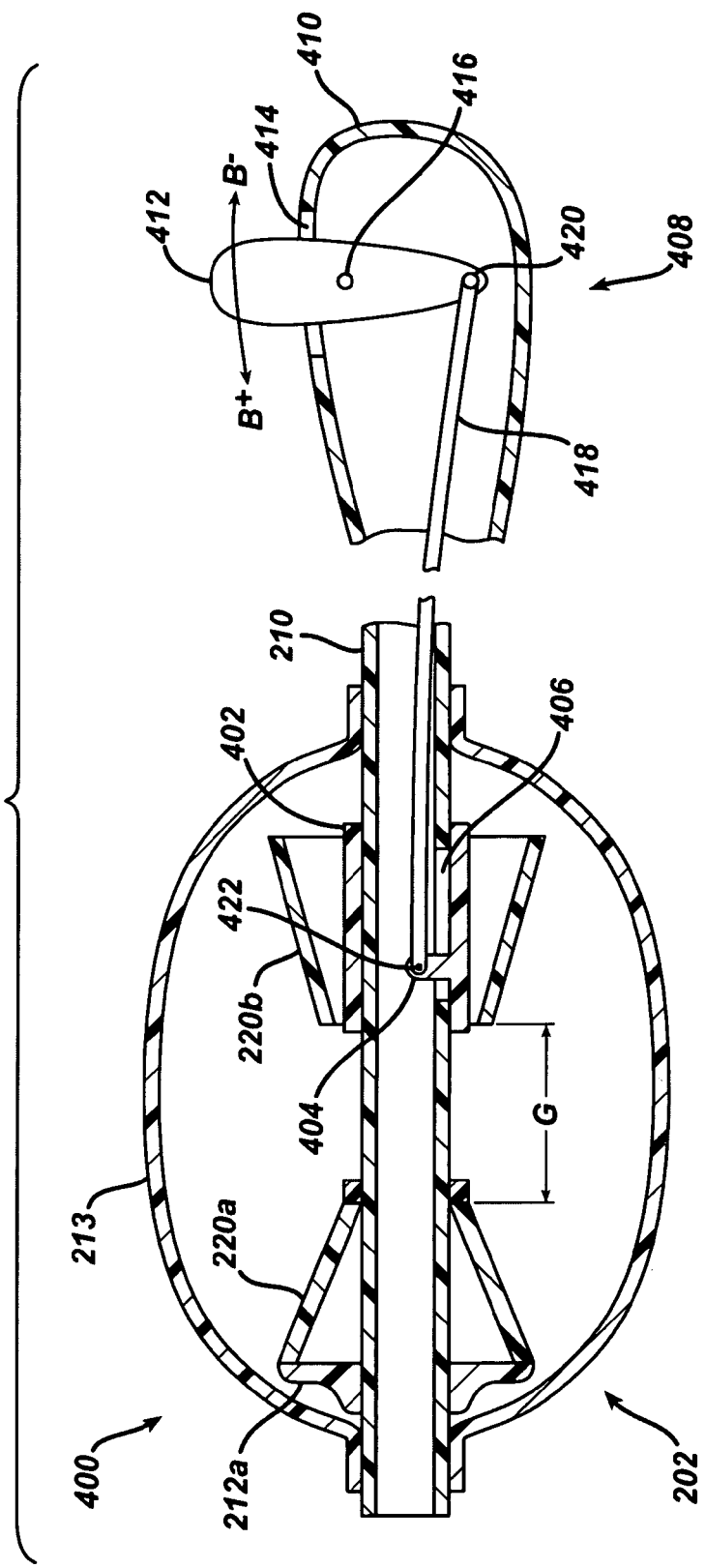
FIG. 7 is a partial section view of an instrument having a means for varying a distance between ultrasonic transducers.

Referring now to FIG. 7, there is shown an instrument having means for varying the length of the gap G between the ultrasonic transducers 220a, 220b, the instrument generally referred to by reference numeral 400. In instrument 400, one of the transducers 220a is fixed as described previously with regard to FIG. 1. However, the other transducer 220b is movable distally towards the fixed transducer 220a and/or proximally away from the fixed transducer 220a to vary the gap G between the transducers 220a, 220b. The movable transducer 220b is preferably mounted on a tubular bearing 402 that is slidingly disposed over the body 210. The tubular bearing includes a projection 404 that projects into an interior of the body 210 through a slot 406. At a proximal end 408 of the instrument 400, or merely at a location proximal to the distal end 202, there is provided a means for controlling the movable transducer 220b to move distally and/or proximally. Preferably, such means comprises a handle 410 having a lever 412 rotatably disposed in the handle 410 through a slot 414 such that a portion of the lever 412 is exterior to the handle 410 and a portion of the lever 412 is interior to the handle 410. The lever 412 is preferably rotatably disposed by way of a pin 416 fixed to the handle 410 and rotatably disposed on the lever 412. A control rod 420 is rotatably disposed at an end of the lever 412 internal to the handle 410 by way of a pin 420. The control rod 418 is preferably disposed in an interior of both the handle 410 and body 210 and rotatably connected to the projection 404 by a pin 422. Operation of the lever 412 in the direction of B+ serves to move the movable transducer 220b proximally to increase the gap G and focus the ultrasound energy at a greater distance $D^2$ while operation of the lever 412 in the direction of B− serves to move the movable transducer 220b distally to decrease the gap G and focus the ultrasound energy at a smaller distance $D^1$. The lever 412 may be biased, such as with a spring (not shown), in either the B− or B+ directions. Furthermore, the lever 412 may be provided with a locking means for locking the lever 412 (and movable transducer 220b) in a predetermined position, such as with a ratchet mechanism (not shown). Still further, the handle 410 and/or lever 412 may be provided with markings (not shown) that indicate the length of the gap G and/or focusing distance D at any given position of the lever 412.

Although, the means for varying the length of the gap G is shown and described as moving one of the ultrasonic transducers 220b and fixing the other 220a, those skilled in the art will appreciate that both ultrasonic transducers 220a, 220b can be moved. Furthermore, although the means for varying the length of the gap G is shown and described as actively moving one of the ultrasonic transducers 220b distally and/or proximally, those skilled in the art will appreciate that the movable ultrasonic transducer 220b may be actively moved in only one direction, such as proximally, and be biased, such as with a spring, in the other direction. Thus, in such a configuration, a cable may be used to actively pull the ultrasonic transducer proximally and locked into a predetermined position. Releasing the ultrasonic transducer from the predetermined position will automatically cause the transducer 220b to move distally under the biasing force of the spring.

Figure 3:
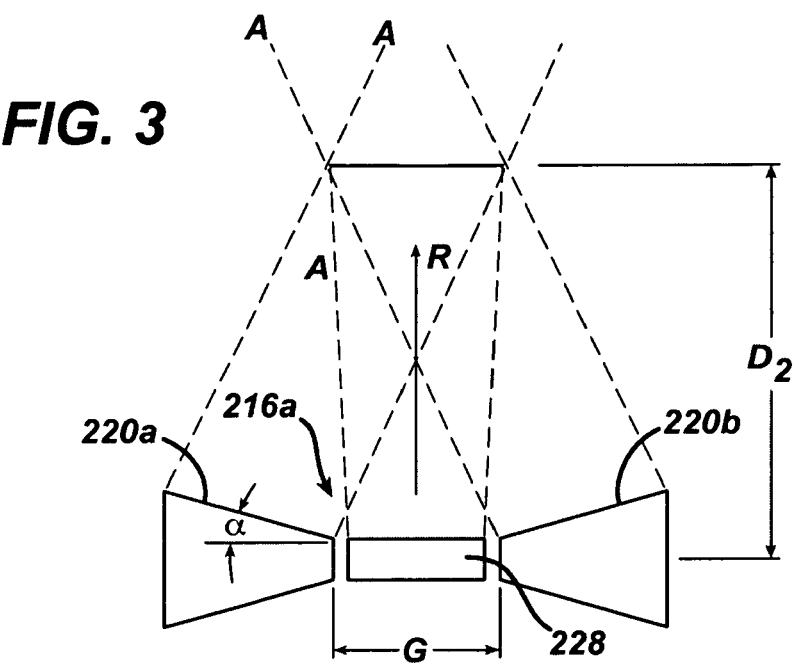
FIG. 3 illustrates a schematic view of an alternative configuration of ultrasonic transducers for the instrument of FIG. 1.

Referring now to FIG. 3, there is shown an alternative ultrasound transducer geometry, generally referred to by reference numeral 216a. As in FIG. 2, the ultrasound transducers in FIG. 3 are shown schematically outside the body 210 for the sake of simplicity. Furthermore, as also discussed previously with regard to FIG. 2, the ultrasonic energy A is shown irradiating in only a single radial direction R for the sake of simplicity. In the alternative ultrasound transducer 216a of FIG. 3, a cylindrical ultrasonic transducer 228 is disposed in the gap G. Therefore, the amount of energy focused at line 226a can be greater than that focused at line 226 of FIG. 2 (assuming all other geometry is the same). However, in order to accommodate the cylindrical ultrasound transducer 228 in the gap G, the length of the gap G may be increased which increases the distance D1 to D2 (assuming all other geometry is the same). Although not necessary, the cylindrical ultrasonic transducer 228 can have a length substantially equal to the length of the gap G.

Figure 4:
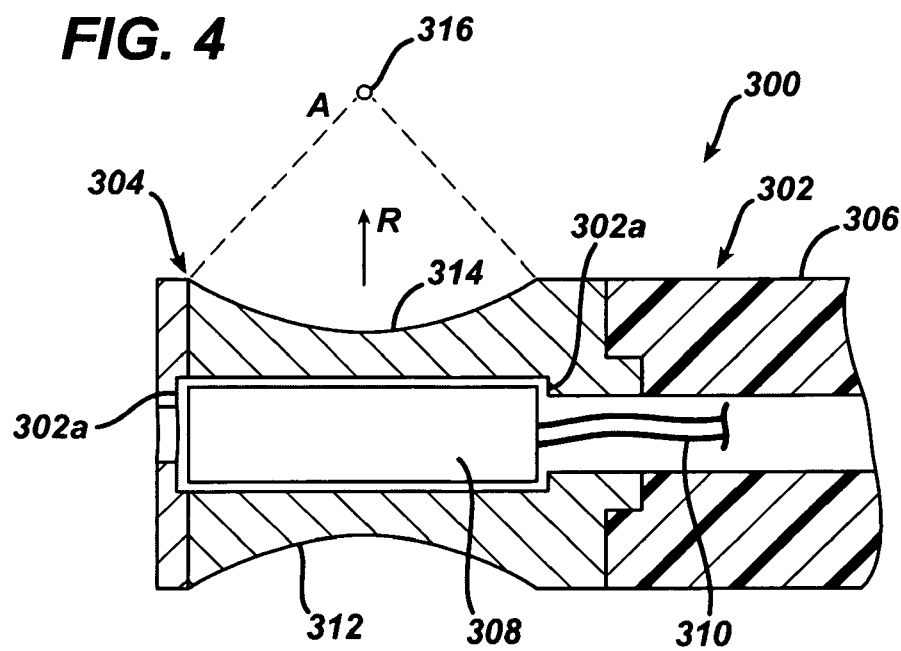
FIG. 4 illustrates another embodiment of a distal end of an ultrasonic instrument.

Referring now to FIG. 4, there is shown a second embodiment of an ultrasonic instrument for ablation of tissue, the ultrasonic instrument being generally referred to by reference numeral 300. Like the ultrasonic instrument 200, the ultrasonic instrument 300 focuses ultrasonic energy A in the radial direction R. The ultrasonic instrument 300 comprises a body 302 which may be formed of a rigid distal portion 304 and a flexible insertion portion 306. The body 302 houses an ultrasonic transducer 308 therein, which may be cylindrically shaped. The cylindrical ultrasonic transducer 308 may be retained in the body 302 by way of stepped portions 302a and/or adhesive. Furthermore, the distal portion 304 of the body 302 may be fastened to the insertion portion 306 by any means known in the art such as by a mechanical crimp or adhesive. The cylindrical ultrasound transducer 308 is operatively connected to an ultrasonic generator (not shown) by way of wiring 310. As discussed above, the ultrasonic generator may be integrally housed in the instrument 300 or remote therefrom.

The ultrasonic instrument 300 further has one or more lenses 312 for focusing ultrasonic energy A from the ultrasonic transducer 308 in the radial direction R. The one or more lenses 312 can be fabricated from any material known in the art for focusing ultrasonic energy, such as aluminum, titanium and some types of plastics. The one or more lenses 312 can be a single concave lens that surrounds the cylindrical ultrasonic transducer 308. Alternatively, the one or more lenses 312 can be a series of concave lenses that surround the cylindrical ultrasonic transducer 308. The one or more lenses 312 may also be convexly shaped depending upon the speed of sound through the material of the lenses 312 relative to the speed of sound through water/tissue. Furthermore, the one or more lenses 312 can be integrally formed with at least a portion of a sidewall of the body 302. However, the one or more lenses 312 can also be separately provided from the body 302.

FIG. 4 illustrates the one or more lenses 312 as having a simple concavity 314 for focusing the ultrasonic energy A in the radial direction R at point 316. Thus, the ultrasonic energy A from the ultrasonic transducer 308 is focused at point 316 in all radial directions (e.g., to form a ring of focused energy). Those skilled in the art will appreciate that other shapes for the one or more lenses 312 are possible, such as multiple concavities, which may be connected with straight sections or concavities having less or more of a curvature. Thus, the focusing of the energy, and the lesions resulted therefrom, can be customized for a particular procedure. Furthermore, the ultrasonic transducers 220, 220b of FIG. 2 may be used in combination with the one or more lenses 312 and/or cylindrical shaped transducers 308 of FIG. 4 to further customize the type of lesions that can be created. Still further, the ultrasonic transducers 220, 220b of FIG. 2 may be used in combination with the one or more lenses 312 and/or cylindrical shaped transducers 308 of FIG. 4 and each can be selectively activated to provide a single instrument capable of forming various types of lesions.

Although the embodiment of FIG. 4 is shown and described as having a rigid distal end, it may also be configured similarly to that shown in FIG. 1 where the conical transducers are replaced with a cylindrical transducer and one or more lenses.

The use of the ultrasonic transducers described above will now be briefly explained with regard to FIG. 1 and by way of example for use in creating lesions in the pulmonary veins of the heart. The distal portion 212, 304 of the ultrasonic instrument 200, 300, preferably in the form of a catheter, is advanced to the left atrium 206 of the heart 208 by any means known in the art, such as by catherization of the heart. The distal portion 212, 304 is inserted into a pulmonary vein 204 of the heart 208 and advanced until proximate an area in which the lesion is desired. The balloon 213 is then expanded by supplying water or saline (or other inflation medium) to the interior of the balloon 213 to fix the distal end of the catheter in the located position. The ultrasonic generator is then operatively connected to the ultrasonic transducers 220a, 220b, 228, 308. The ultrasonic energy A produced by the transducers 220a, 220b, 228, 308 is focused according to the geometry of the transducers, lenses, and/or arrangement of the transducers relative to each other to create one or more lesions on the inner surface of the pulmonary vein 304. The balloon 213 is then deflated and the procedure is repeated as necessary in other pulmonary veins. Such lesion patterns have been found to be beneficial in controlling cardiac arrhythmias, particularly atrial fibrillation.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An ultrasonic instrument for ablation of tissue, the ultrasonic instrument comprising at least two truncated cone-shaped ultrasonic transducers having truncated ends arranged to face each other, the ultrasonic transducers shaped to focus ultrasonic ablational energy therefrom in a radial direction.

2. The ultrasonic instrument of claim 1, wherein the truncated ends are separated by a predetermined distance to form a gap.

3. The ultrasonic instrument of claim 2, further comprising a cylindrical ultrasonic transducer disposed in the gap.

4. The ultrasonic instrument of claim 3, wherein the cylindrical ultrasonic transducer has a length substantially equal to the predetermined distance.

5. The ultrasonic instrument of claim 1, wherein the truncated ends are separated by a variable distance to form a gap.

6. The ultrasonic instrument of claim 1, wherein the at least two ultrasonic transducers comprises two ultrasonic transducers separated by a gap and wherein the ultrasonic instrument further comprises means for varying the length of the gap.

7. An ultrasonic instrument for ablation of tissue, the ultrasonic instrument comprising: a body having a distal end;
   at least two truncated cone-shaped ultrasonic transducers having truncated ends arranged to face each other, the at least two ultrasonic transducers being shaped to focus ultrasonic ablational energy therefrom in a radial direction; and
   an ultrasonic generator operatively connected to provide ablational energy to the at least two ultrasonic transducers.

8. An ultrasonic instrument comprising:
   a body having a distal end; and
   at least two truncated cone-shaped ultrasonic transducers having truncated ends arranged to face each other, the at least two ultrasonic transducers being shaped to focus ultrasonic ablational energy therefrom in a radial direction.

9. A method for ablating tissue with ultrasonic energy, the method comprising:
   generating ultrasonic energy for ablation from at least two truncated cone-shaped ultrasonic transducers having truncated ends arranged to face each other; and
   focusing the ultrasonic energy from each of the ultrasonic ablational transducers in the radial direction.

10. The method of claim 9, further comprising separating the truncated ends by a predetermined distance to form a gap.

11. The method of claim 10, further comprising disposing a cylindrical ultrasonic transducer in the gap.

12. The method of claim 10, further comprising varying the distance between the truncated ends.

13. The method of claim 9, further comprising inserting at least a portion of the ultrasonic transducers into a pulmonary vein of the heart prior to or simultaneous with the generating.

14. The method of claim 13, wherein the ultrasonic transducers are enclosed in an inflatable balloon, the method further comprising inflating the balloon to fix the ultrasonic transducers in a predetermined position in the pulmonary vein.

15. The method of claim 9, further comprising varying the distance to which the ultrasonic energy is focused in the radial direction.

* * * * *